United States Patent
Teicher et al.

(10) Patent No.: US 8,078,253 B2
(45) Date of Patent: Dec. 13, 2011

(54) COMPUTERIZED METHODS FOR EVALUATING RESPONSE LATENCY AND ACCURACY IN THE DIAGNOSIS OF ATTENTION DEFICIT HYPERACTIVITY DISORDER

(75) Inventors: Martin H. Teicher, Brookline, MA (US); Steven B. Lowen, Burlington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 2202 days.

(21) Appl. No.: 10/370,809

(22) Filed: Feb. 20, 2003

(65) Prior Publication Data

US 2003/0233032 A1    Dec. 18, 2003

Related U.S. Application Data

(60) Provisional application No. 60/358,953, filed on Feb. 22, 2002.

(51) Int. Cl.
*A61B 5/05*    (2006.01)

(52) U.S. Cl. ........................................ 600/407; 128/898

(58) Field of Classification Search .................. 600/383, 600/384, 558, 300, 595; 128/898
See application file for complete search history.

(56) References Cited

U.S. PATENT DOCUMENTS

| | | | |
|---|---|---|---|
| 4,987,903 A * | 1/1991 | Keppel et al. .................. 600/545 |
| 5,011,413 A | 4/1991 | Ferris et al. .................... 434/358 |
| 5,150,716 A * | 9/1992 | Franssen et al. ............... 600/587 |
| 5,295,491 A * | 3/1994 | Gevins .......................... 600/544 |
| 5,334,324 A * | 8/1994 | Zeise et al. .................... 510/513 |
| 5,344,324 A | 9/1994 | O'Donnell et al. ........... 434/258 |
| 5,778,893 A * | 7/1998 | Potter ............................ 128/898 |
| 5,801,810 A * | 9/1998 | Roenker ....................... 351/246 |
| 5,913,310 A * | 6/1999 | Brown .......................... 128/897 |
| 5,940,801 A | 8/1999 | Brown |
| 6,030,226 A * | 2/2000 | Hersh ........................... 434/236 |
| 6,053,739 A * | 4/2000 | Stewart et al. ................ 434/236 |
| 6,067,986 A * | 5/2000 | Kluger et al. ................. 600/595 |
| 6,113,538 A * | 9/2000 | Bowles et al. ................ 600/300 |
| 6,206,700 B1 * | 3/2001 | Brown et al. ................. 434/116 |
| 6,241,686 B1 | 6/2001 | Balkin et al. ................. 600/544 |
| 6,280,198 B1 * | 8/2001 | Calhoun et al. .............. 434/236 |
| 6,283,761 B1 * | 9/2001 | Joao ............................. 434/236 |
| 6,306,086 B1 * | 10/2001 | Buschke ....................... 600/300 |
| 6,416,480 B1 * | 7/2002 | Nenov .......................... 600/557 |
| 6,435,878 B1 * | 8/2002 | Reynolds et al. ............. 434/236 |
| 6,475,161 B2 * | 11/2002 | Teicher et al. ................ 600/558 |

(Continued)

FOREIGN PATENT DOCUMENTS

| | | |
|---|---|---|
| EP | 1122679 | 8/2001 |
| WO | WO 02/078536 | 10/2002 |

OTHER PUBLICATIONS

Teicher et al. Objective Measurement of Hyperactivity and Attentional Problems in ADHD. J. Am. Acad. Child Adolesc. Psychiatry, 35(3):334-342, Mar. 1996.*

(Continued)

*Primary Examiner* — Parikha Mehta
(74) *Attorney, Agent, or Firm* — Clark & Elbing LLP

(57) ABSTRACT

Provided are methods for diagnosing the presence, type, or severity of a dementia in a human subject. The methods involve using a computer-based system to assess impairment of certain cognitive and motor functions that are indicative of Alzheimer's disease and other forms of dementia.

29 Claims, 2 Drawing Sheets

U.S. PATENT DOCUMENTS

| | | | |
|---|---|---|---|
| 7,211,050 B1 * | 5/2007 | Caplygin | 600/558 |
| 2001/0024512 A1 * | 9/2001 | Yoronka et al. | 382/103 |
| 2001/0056477 A1 * | 12/2001 | McTernan et al. | 709/219 |

OTHER PUBLICATIONS

Egan De. Characterizing Spatial Ability: Different Mental Processes Reflected in Accuracy and Latency Scores. Aug. 1978.*

Greenberg, "An objective measure of methylphenidate response: clinical use of the MCA," *Psychopharmacol. Bull.* 23(2):279-282 (1987).

Paulus et al., "The effects of MDMA and other methylenedioxy-substituted phenylalkylamines on the structure of rat locomotor activity," *Neuropsychopharmacology* 7(1):15-31 (1992).

Rosvold et al., "A continuous performance test of brain damage," *J. Consulting and Clinical Psychology* 20(5):343-350 (1956).

Teicher et al., "Objective measurement of hyperactivity and attentional problems in ADHD," *J. Am. Acad. Child Adolesc. Psychiatry* 35(3):334-342 (1996).

Darby et al. "Mild Cognitive Impairment can be Detected by Multiple Assessments in a Single Day," Neurology, 59:1042-1046, 2002.

Sereno et al. "Spatial Selective Attention in Schizophrenic, Affective Disorder, and Normal Subjects," Schizophrenic Research, 20:33-50, 1996.

Dennis E. Egan, "Characterizing Spatial Ability: Different Mental Processes Reflected in Accuracy and Latency Scores," *Naval Aerospace Medical Research Laboratory Pensacola FL.*, Aug. 1-31, 1978.

* cited by examiner

COMPUTERIZED METHODS FOR EVALUATING RESPONSE LATENCY AND ACCURACY IN THE DIAGNOSIS OF ATTENTION DEFICIT HYPERACTIVITY DISORDER

CROSS REFERENCE TO RELATED APPLICATIONS

This application claims priority from U.S. Provisional Application Ser. No. 60/358,953, filed Feb. 22, 2002.

FIELD OF THE INVENTION

The invention relates to methods of performing continuous performance testing.

BACKGROUND OF THE INVENTION

Continuous performance testing, in various forms, has become a standard clinical procedure. Generally speaking, continuous performance testing tests a subject's visual attention by displaying a series of visual stimuli, to which the subject is instructed to respond. In the typical (and simplest) case, often referred to as a "Go—No Go" test, the stimuli are of two types (the "Go" and "No Go" stimuli); the subject is instructed to respond only to the "Go" stimulus, and not to respond or "pass" when presented with the "No Go" stimulus. Data collected for each stimulus presented consists of the type of the stimulus; whether or not the subjects responded; and, if so, how long they took to respond. The continuous performance test has been in use since the 1950s (see "A continuous performance test of brain damage," Rosvold et al. (1956), *J. Consulting and Clinical Psychology* 20:343-350), with computerized versions available in the 1970s and 1980s (see, e.g., "An objective measure of methylphenidate response: clinical use of the MCA," Greenberg (1987), *Psychopharmacol. Bull.* 23:279-282.

While these tests provide raw data for continuous performance testing, they have typically distilled the data into a few isolated numbers, such as: Latency (the average of all response times to "Go" stimuli); Commission Errors (the number responses to "No Go" stimuli divided by the total number of "No Go" stimuli); and Accuracy (percentage correct; the correct passes to "No Go" stimuli, added together and divided by the total number of stimuli). These previous methods of analysis fail to account for a wide range of normal strategies. For example, a subject might elect to be careful, favoring accuracy over speed. Another subject could choose to be as fast as possible, willing to commit more errors in the process. Some methods do not take such strategies into account.

Alzheimer's disease ("AD") is a degenerative brain disorder that afflicts millions of people worldwide. It is the most common form of dementia and can affect memory, mood, personality, and cognitive ability. The risk of developing AD becomes greater with age. As the average human life-span continues to increase, the number of people developing AD at some point in their lives is escalating rapidly. Currently, an estimated 1 in 20 people over the age of 65 are affected by some form of dementia. In persons over the age of 80, that number rises to 1 in 5.

The effects of AD can be devastating. Early symptoms include forgetfulness, learning difficulties, and loss of concentration. The later stages of the disease are characterized by disorientation, extreme memory loss, impairment of speech and reading comprehension, and changes in personality. Dramatic mood swings can occur, including outbursts of anger, bouts of fearfulness, and periods of deep apathy or depression. The sufferer becomes increasingly confused, particularly when confronted with unfamiliar settings, and may wander off and become lost. Physical problems, such as an odd gait, a loss of coordination, an inability to chew and swallow, and an inability to control bowel and bladder functions, gradually develop. Eventually, the patient may become totally noncommunicative, physically helpless, and incontinent. The disease is invariably fatal.

AD can also have a profound impact on the relatives of the person suffering from the disease. About seventy percent of AD patients are cared for at home by family members. In the early and middle stages of AD, patients may need help in managing their financial and business affairs. As the disease progresses, the affected person becomes steadily more dependent on caregivers to help perform daily tasks. The patient's mental functioning eventually deteriorates to the point where it is not safe to leave the person unattended. Ultimately, the disease may leave its victims bedridden and unable to care for themselves. Under these circumstances, AD can take a tremendous physical, financial, and emotional toll on the caregivers.

Although there is currently no cure for AD, early diagnosis is important for a number of reasons. For instance, it is crucial to rule out other conditions which have symptoms that are similar to AD, but which are treatable. In addition, the patient and family members can receive much help and advice from doctors and other professionals in coping with this disease. Furthermore, medications are available which can help relieve some of the common symptoms of AD, including depression, anxiety, and sleep disturbance. There is also hope that treatments may be developed in the future which will slow or halt the progression of the disease, making early detection and intervention even more vital.

Diagnosing AD can often be difficult, especially in the early stages, because many of the symptoms of the disease mirror the natural signs of aging. In some situations, a definitive diagnosis may not be possible until the patient has died and an autopsy can be performed. There are also several forms of dementia that appear superficially similar to AD, but have distinct underlying pathological processes. These dementias are often indistinguishable from AD using conventional testing techniques.

Current psychological tests for AD that are used clinically focus on deteriorations in memory, particularly in short-term or "working" memory. In general, the disorder must be fairly well advanced before significant impairments in memory are observed. Consequently, these tests are not fully capable of diagnosing AD in the early stages. Thus, there is a need for an easily administered, non-invasive, and reliable test for detecting AD while still in the early stages of development. In particular, there is a need for a reliable continuous performance test for detecting AD that takes into account a subject's rational preferences.

SUMMARY OF THE INVENTION

The regions of the brain that mediate working memory also regulate the capacity for sustained attention (i.e., vigilance), control of impulses, and motor activity. We believe that, in patients suffering from AD and other dementias, impairment of these functions often occurs prior to detectable changes in memory. We posit that testing a patient for disturbances in attention, impulsiveness, and/or motor function can lead to early diagnosis of AD and other forms of dementia. Earlier diagnosis, in turn, makes it possible to begin treating the underlying disorder while still in the early stages, in order to halt or slow its progression.

Accordingly, the present invention provides a method of diagnosing the presence, type, or severity of a dementia in a human subject using computerized testing, which method includes the steps of: (a) placing, in proximity to the subject, a monitor that is connected to a computer, and a device that is controllable by the subject and that is also connected to the computer; (b) presenting the subject with instructions for activating the device in response to visual images on the monitor; (c) presenting to the subject one or more visual images on the monitor; (d) storing in the computer the instances of device activation by the subject; (e) determining an accuracy of device activation; (f) determining a response time of device activation; and (g) assigning a test statistic, wherein certain values indicate normal test results and other values indicate abnormal test results.

In another embodiment of the invention, the method alternatively includes the step of: (g) calculating an adjusted latency. In yet another embodiment, the method of the invention includes the step of: (g) calculating an adjusted accuracy.

In other embodiments, the method of the invention includes: (h) using a motion analysis device connected to said computer to record movements of said subject during presentation of said visual images; (i) storing the record of said movements in said computer; (j) analyzing said recorded movements for deviations from pre-determined norms; and (k) using the analysis of step (j) together with the test statistic, the adjusted latency, and/or the adjusted accuracy to diagnose ADHD or a form of dementia. The motion analysis device is preferably an infrared camera capable of detecting small infrared reflective markers. These markers can be placed at various positions on the subject, such as the head, elbow, and shoulders, in order to monitor the movements of these portions of the subject's body.

The method of the invention can be used to diagnose and distinguish various forms of dementia, including dementia associated with Alzheimer's disease, frontotemporal degenerative dementias (e.g., Pick's disease, corticobasal ganglionic degenerations, and frontotemporal dementia), Huntington's disease, Creutzfeldt Jakob disease, Parkinson's disease, cerebrovascular disease, head trauma, and substance abuse).

Other features and advantages of the invention will be apparent from the following detailed description and from the claims.

DETAILED DESCRIPTION

Figure 1:
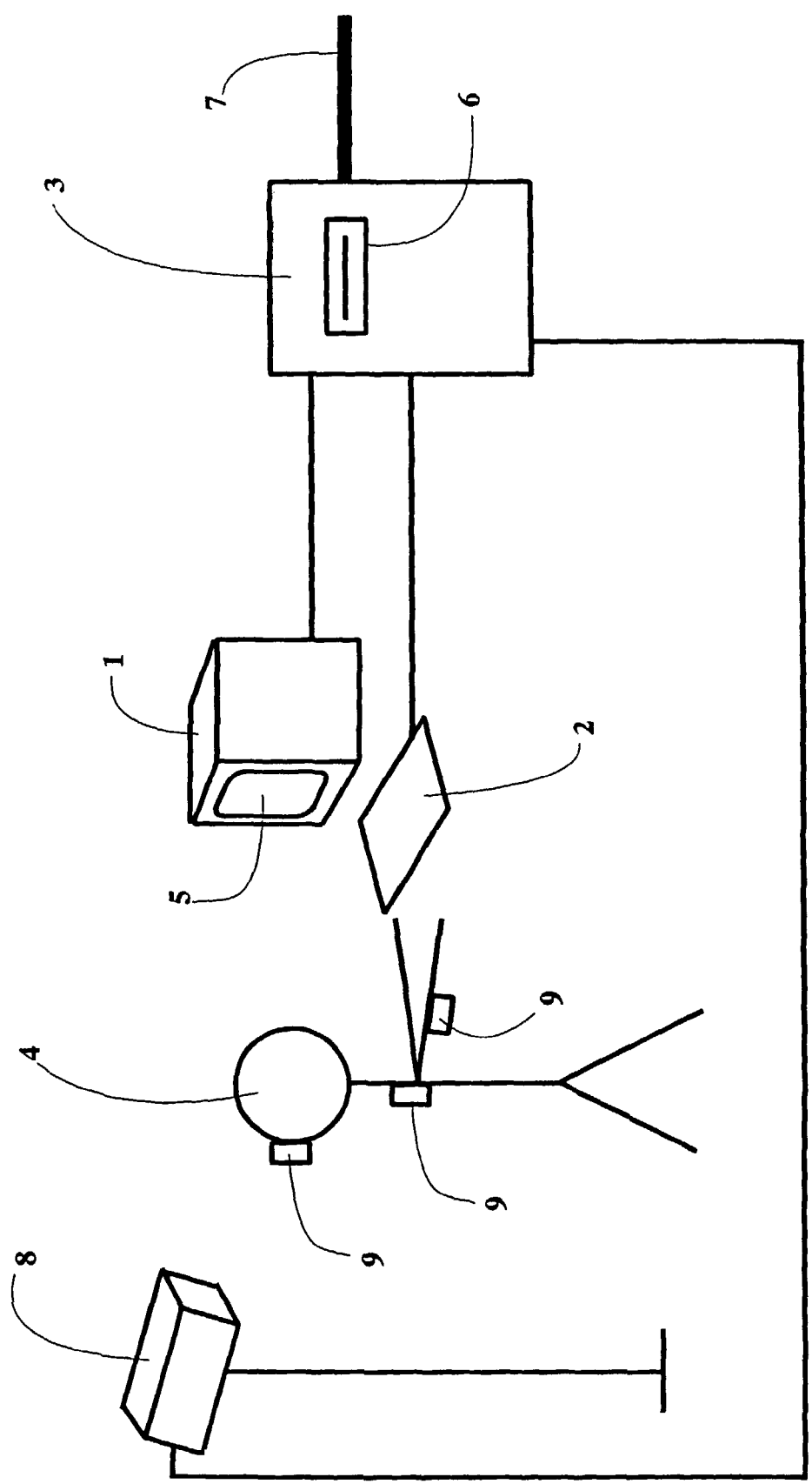
FIG. 1 is a schematic diagram illustrating a computerized system that provides diagnostic information for assessing the presence or degree of a dementia.

The present invention features a method for diagnosing the presence or severity of a dementia in a human subject. The method utilizes a computer-based system to assess impairment of certain cognitive and motor functions that are indicative of AD and other forms of dementia. The method of the invention can be used for detecting ADHD and other types of abnormal behavior.

An embodiment of a system for performing a method of the invention is shown in the Figure. The system includes a monitor 1 that is a capable of displaying visual images on a screen 5. The monitor 1 is attached to a computer 3 and is positioned in proximity to a subject 4, so that the subject 4 may view the images displayed on the monitor screen 5. The computer 3 can be programmed to display a desired sequence of images, to which the subject 4 is instructed to respond by activating an input device 2 that is also attached to the computer 3 and is controllable by the subject 4. The input device 2 can be, for example, a standard computer keyboard, a hand-held plunger switch, or a large, easy-to-hit switch several (2-3) inches in length. When activated, the input device 2 sends the subject's inputs to the computer 3 which stores and analyzes the incidents of device activation.

The system may also include a motion analysis device 8 that is connected to the computer 3 and positioned so as to record the movements of the subject 4. Any video camera or other motion-sensing device capable of detecting the movements of the subject 4 can be used. For instance, the motion analysis device 8 can be an infrared motion analysis system (e.g., Qualisys, Glastonbury, Conn.) that includes a high-resolution CCD infrared video camera, an infrared strobe, and a video processor that provides hardware analysis of the video signal and outputs data to the computer 3. Such infrared motion analysis systems are known in the art, and are specifically designed to detect and record the precise vertical and horizontal position of small, light-weight infrared reflective markers 9. These markers 9 are attached to the subject 4 at various points, such as the head, shoulders, and elbows. As the subject 4 moves these portions of his or her body, the IR motion analysis system detects changes in the positions of the markers 9 and relays this information to the computer 3. Successive marker coordinates can be stored in the computer 3 and analyzed using commercially available software (e.g., OPTAX software, OptaxSystems, Inc., Burlington, Mass.).

The computer 3 can be a stand-alone personal computer, preferably with high computational capacity microprocessors. Alternatively, a minicomputer or mainframe computer can be used. The computer 3 can have a disc drive 6 into which the software that analyzes the subject's input's and/or movement patterns is loaded. In a preferred embodiment, the computer 3 has a connection 7 to a network of computers, such as a global computer network. This allows the computer 3 to exchange data with other computers connected to the network. In other preferred embodiments, the computer network is a local area network, a wide area network, an intranet, or an extranet. Thus, a subject may be tested not only in a clinical setting, but also at a remote location, such as the home, school, or workplace, thereby eliminating the inconvenience of traveling long distances for testing.

The system of the invention can be used to test certain cognitive and psychomotor functions that are diagnostic of AD and other forms of dementia. For instance, the capacity for sustained attention, control of impulses, reaction time, and regulation or inhibition of motor activity may be impaired in patients suffering from dementia. Thus, by measuring these functions it is possible to distinguish normal patients from those with dementia, and even identify the type of dementia the patient is experiencing. The system can also be used to monitor these functions at different stages of the disease in order to track its development and progression.

Attention and Reaction Time

One way the system can be used to assess attention and reaction time is by providing the subject with a continuous performance task ("CPT") and recording the subject's performance. A typical CPT involves presenting the subject with a series of stimuli and instructing the subject to respond only to certain target stimuli. The subject's performance is scored based on the number of target stimuli correctly identified, the number of target stimuli missed, the number of responses to non-target stimuli, the number of non-target stimuli correctly missed, and the response time (e.g., U.S. Pat. No. 5,940,801).

For example, a subject's visual attention can be tested by displaying a series of visual stimuli on a computer screen, for which different responses are required of the subject. The stimuli can be any sort of visual image, including but not limited to, individual symbols, numbers, letters, or shapes, or a combination thereof. In one version of this test, the images are of two types and the subject is instructed to respond to only one type by activating the input device when the target stimuli appears on the screen. Typically, the test requires the subject to distinguish between two similar visual images, such as a five-pointed star and an eight-pointed star (see, e.g., Greenberg (1987), *Psychopharmacol. Bull.* 23:279-282 and Rosvold et al. (1956), *J. Consulting and Clinical Psychology* 20:343-350). For instance, the subject is instructed to press the space bar on the computer's keyboard if an eight-pointed star is displayed on the computer screen, and to do nothing when a five-pointed star appears on the screen. Data are collected for each individual image presentation, including the type of stimulus (e.g., five-pointed star or eight-pointed star), whether or not the subject responded, and, if so, the amount of time the subject took to respond. From this raw data, the percentage of correct responses to the target stimulus, percentage of correct passes to the non-target stimulus, average response time, response time variability, and other statistics may be obtained. In addition, as is discussed below, a motion analysis device can be used to detect and record the subject's movement patterns throughout the test. At the end of the test, the recorded data (e.g., key press information and movement information) can be processed by the computer or transmitted over a computer network to a central processing station, where a report is generated and transmitted back to the testing site (e.g., U.S. Ser. No. 60/243,963).

Another CPT for assessing a subject's visual attention capabilities involves measuring the duration of time a particular visual stimulus must be present after a period of no stimulus before a subject can detect and respond to it (e.g., U.S. Pat. No. 5,801,810). For example, overall reaction time is estimated by presenting either a particular shape, such as a circle, or no stimulus (i.e., a blank screen) in random fashion. The subject is instructed to activate the input device as soon as possible after the circle appears on the screen, but not before. For both circle and no stimulus presentations, the percentage correct, the average response time, and variations about that average are stored, and provide a means for assessing deterioration in visual attention (See U.S. Ser. No. 60/204,663).

Figure 2:
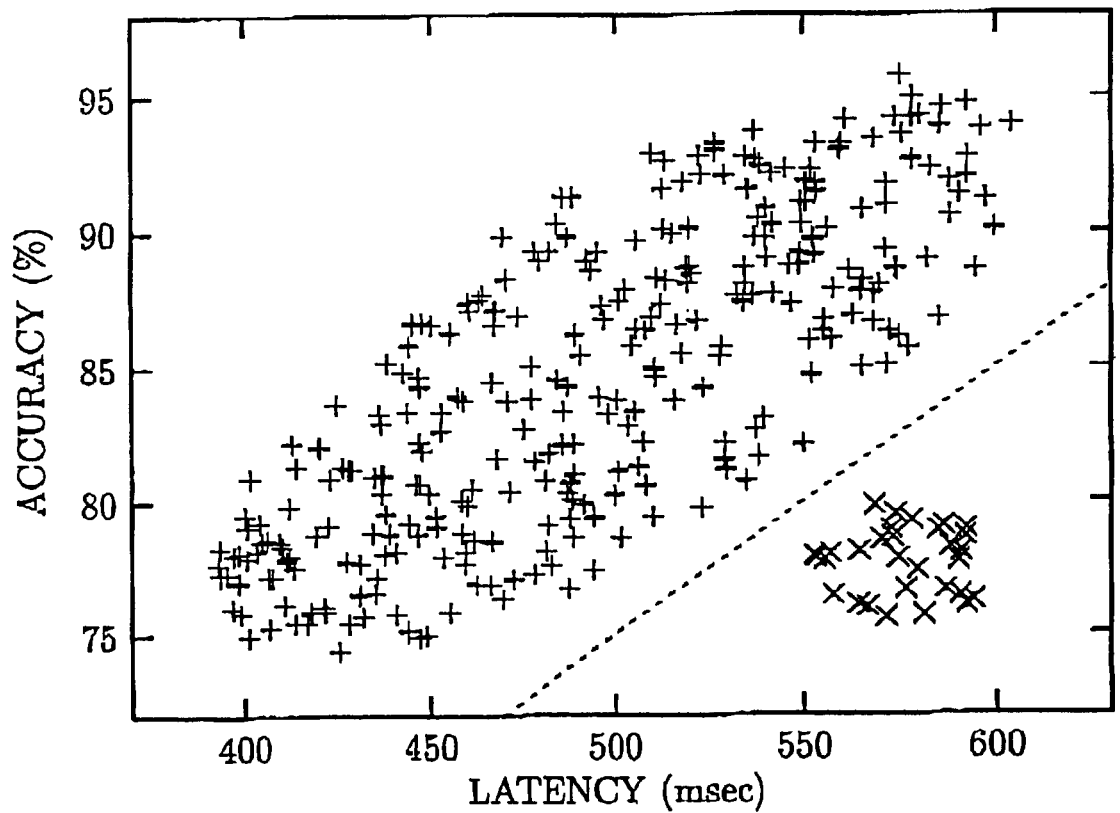
FIG. 2 is a graphical representation of theoretical continuous performance test results for a group of subjects.

These CPTs may be used alone, together, or in conjunction with other well-known psychological tests for determining accuracy and reaction time (or "latency"). The methods of the invention allow interpretation and analysis of data by taking a wide range of normal strategies into account. For example, methods of the invention permit identification of a normal subject who elects to be careful and favors accuracy over speed. The invention also allows for identification of a normal subject who attempts to be as fast as possible and is willing to commit more errors in the process. Normative values for speed and accuracy have to take all possibilities into account, and therefore yield large ranges. For example, consider a theoretical continuous performance test and group of subjects for which accuracies range from about 75 to 95%, with response times simultaneously ranging from about 400 to 600 msec, as shown in FIG. 2. This procedure is exemplified with theoretical data in order to simplify the following explanation, and also to protect patient confidentiality. However, the method works quite well with real data, although not perfectly, and the explanation would be much more complex. The data shown in FIG. 2 resemble real data, and illustrate the same points.

FIG. 2 is a graphical representation of theoretical continuous performance test results for a group of subjects. FIG. 2 shows values for latency in msec (horizontal axis) and accuracy in % (vertical axis) for normal subjects ("plus signs" [+]) and abnormal subjects ("crosses" [X]). Different normal subjects use different strategies, yielding, for example, high speed (low latency), high accuracy, or a compromise of the two. Thus, a large range of latencies and accuracies fall within the normal range of behaviors. As a consequence, neither latency nor accuracy alone can discriminate between normal and abnormal subjects. However, a composite measure, such as the simple linear relationship (dashed line) shown in FIG. 2 is able to distinguish between the two groups perfectly.

As shown in FIG. 2, normal responses typically range from 400 msec and 75% to 600 msec and 95%; faster responses tend to be less accurate. A test result of 580 msec and 78% accuracy indicates abnormal results, however, since this subject is both relatively slow and relatively inaccurate. However, for this subject the individual scores for speed and accuracy lie within their respective normative ranges, falsely indicating normal behavior. Here latencies lie in the range 393-604 msec for normal data, and 553-594 msec for abnormal data; accuracies lie in the range 74.4-95.7% for normal data, and 75.6-79.8% for abnormal data. In both cases, all abnormal data values lie within the difficult ranges for normal data.

In a preferred embodiment, the invention uses a combined speed/accuracy score, which takes into account both scores in determining normative values and discriminating between normal and abnormal results. This discriminant, represented in FIG. 2 by a dashed line, follows the equation:

$$\text{Accuracy}=25+\text{Latency}/10 \quad (1)$$

where accuracy is in percent (%), and latency is in msec. Following this theoretical example, given an average latency and overall accuracy, a test statistic is obtained as follows:

$$T=\text{Accuracy}-(25+\text{Latency}/10) \quad (2)$$

Positive values of T indicate normal behavior, while negative values of T indicate abnormal behavior. This test statistic will assign normal and abnormal status to all subjects perfectly, which is impossible for any test statistic derived from either latency or accuracy alone.

In addition to generating a useful test statistic, the method of the invention may be used to generate an accuracy-adjusted latency score. For example, we could pick 85% as a typical accuracy, and adjust the actual latency accordingly. Rearranging Eq. 1 provides $$\text{Adj. Latency}=\text{Latency}-10\times(\text{Accuracy}-85) \quad (3)$$

Applying this transformation to the data yields adjusted latencies of 422-579 msec for normal data, and 620-682 msec for abnormal data. (Compare this with the overlapping ranges obtained for non-adjusted latency: 393-604 for normal, and 553-594 for abnormal.) Thus a discriminating value of 600 msec for accuracy-adjusted latency would perfectly separate normal and abnormal subjects.

Similarly, it is possible to generate a latency-adjusted accuracy score, which would enjoy similar properties. For example, the latency-adjusted accuracy score may be determined using the following equation:

$$\text{Adj. Accuracy}=\text{Accuracy}+10\times(\text{Latency}-R) \quad (4)$$

wherein R represents the typical latency. This could result in adjusted accuracy scores in excess of 100%.

Methods of the invention yield much better discrimination between normal and abnormal behavior because the invention simultaneously incorporates the effects of two test variables in a coordinated manner. The invention may also be used to adjust one test variable by means of the other, to yield scores which may be directly compared among different subjects who nevertheless use different test strategies.

In further embodiments of the invention, other monotonic functions as discriminants or adjustment criterion can be used. For example, if the normal data shown in FIG. 2 were instead curved, and resembled the lower case letter "r," a similarly curved line separating the normal from abnormal test results would have to be used. This could also be used in a formula to adjust latency based on accuracy or vice versa, as in Eq. 3.

In addition, age and gender effects may be taken into account in the practice of the invention, as both will have an effect on test scores.

The method of the invention can also be applied to latency and commission errors. In this case, however, decreased latency likely will least to increased commission errors, so that normal test data would follow a line from upper left to lower right, and have a negative slope. The method of the invention can also be applied to other pairs of test scores, or even to three or more test scores as a group. For example, using three variables would yield a plane or curved surface as a discriminant, and a score adjusted by the other two variables.

Motor Activity

Using the system of the invention, the movement abnormalities of a person with AD can be objectively discerned by measuring the frequency, amplitude, and pattern of body movements. As discussed above, very precise measurements of a subject's movements can be made using a motion analysis system that includes an infrared camera and one or more infrared reflective markers placed on the subject. These systems typically have a high spatial resolution (e.g. 40 µm) and can simultaneously track the vertical and horizontal movements of as many as 20 IR reflective markers. By using multiple IR cameras, it is possible to track the three-dimensional movements of the markers, if so desired.

Generally, the motor activity of the subject is monitored during performance of a CPT, such as those described above. Data is collected and sent to a computer to determine the time spent moving, number of movements, total distance and area traveled, and certain spatiotemporal measures of movement complexity. The computer, in addition to including the software required for running the CPT, contains software that performs the processing and analysis of the movement data (e.g. OPTAX Software).

Movement patterns of the subject can be analyzed using, for example, the procedures described in Paulus, M., Geyer, M. (1992), *Neuropsychopharmacology* 7:15-31 and Teicher et al. (March 1996), *J. Am. Acad. Child Adolsec. Psychiatry* 35(3): 334-342, which are based on the concept of microevents. A new microevent begins whenever the marker moves more than a predetermined distance (e.g., 1.0 mm or more) from the location of the previous microevent, and is defined by its position and duration. From the sequence of microevents, the mean locomotor path length can be calculated, along with two scaling exponents. The first exponent, the spatial scaling exponent, is a measure of the complexity of the movement and is calculated by ascertaining the logarithmic rate of information decay at progressively lower levels of resolution. Conceptually, if a marker is still or moving in a straight line, no information is lost if the marker's position is sampled less frequently. The total distance traversed can still be calculated. On the other hand, if a marker is moving in a convoluted path, then less frequent sampling smoothes out the route and underestimates the distance traveled. Spatial complexity corresponds to the concept of fractal dimensions and ranges from 1.0 (straight line movement) to 2.0 (complex, convoluted movement patterns).

The other exponent, known as the temporal scaling exponent, is calculated from the log-log relationship between the frequency of the microevents and their duration. For a two-process model in which a marker is either in motion or immobile, stochastic theory dictates that there will be a greater number of brief periods of immobility than long periods of immobility (though not necessarily a greater amount of time). The log-log relationship provides a robust measure of relative activity versus inactivity and indicates the degree to which a subject is moving in the environment.

Since humans suffering from dementia exhibit abnormal motor activity and impaired cognitive functioning, the data collected concerning a subject's movement patterns and CPT performance can be compared to those of demented and non-demented patients to determine whether the subject has dementia. If so, the data can be used to ascertain not only the severity of the dementia, but also its etiology, thereby allowing the attending physician to determine the most appropriate course of treatment.

Other Embodiments

Although the present invention has been described with reference to preferred embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention described herein.

All publications, patents, and patent applications mentioned in this specification are hereby incorporated by reference.

What is claimed is:

1. A method of diagnosing Attention Deficit Hyperactivity Disorder in a subject, said method comprising the steps of:
   (a) placing, in proximity to a subject, (i) a monitor that is connected to a computer, and (ii) a device that can be activated by said subject and that is also connected to said computer;
   (b) presenting to said subject instructions with respect to activating said device in response to visual images on said monitor, wherein said subject is instructed to activate said device when a specified image is displayed on said monitor;
   (c) presenting to said subject said visual images on said monitor while recording instances of device activation by said subject;
   (d) storing in said computer the instances of device activation by said subject;
   (e) determining an accuracy parameter of device activation;
   (f) determining a response time parameter of device activation;
   (g) calculating a test value based on (e) and (f) as follows:

$$T=(\text{accuracy})-[25+\text{response time}/10)],$$

wherein a positive value of T indicates a normal test result and a negative value of T indicates an abnormal test result characteristic of Attention Deficit Hyperactivity Disorder; and (h) using the calculation of step (g) to generate a report of said results.

2. A method of diagnosing Attention Deficit Hyperactivity Disorder in a subject, said method comprising the steps of:
   (a) placing, in proximity to a subject, (i) a monitor that is connected to a computer, and (ii) a device that can be activated by said subject and that is also connected to said computer;
   (b) presenting to said subject instructions with respect to activating said device in response to visual images on said monitor, wherein said subject is instructed to activate said device when a specified image is displayed on said monitor;
   (c) presenting to said subject said visual images on said monitor while recording instances of device activation by said subject;
   (d) storing in said computer the instances of device activation by said subject;
   (e) determining an accuracy parameter of device activation;
   (f) determining a response time parameter of device activation;
   (g) calculating an Adjusted Latency as follows:

Adjusted Latency=(response time)−10×(accuracy−$Q$), where the value of Q is selected to represent a typical accuracy value, and wherein the adjusted latency discriminates between normal test results and abnormal test results characteristic of Attention Deficit Hyperactivity Disorder; and
   (h) using the calculation of step (g) to generate a report of said results.

3. A method of diagnosing Attention Deficit Hyperactivity Disorder in a subject, said method comprising the steps of:
   (a) placing, in proximity to a subject, (i) a monitor that is connected to a computer, and (ii) a device that can be activated by said subject and that is also connected to said computer;
   (b) presenting to said subject instructions with respect to activating said device in response to visual images on said monitor, wherein said subject is instructed to activate said device when a specified image is displayed on said monitor;
   (c) presenting to said subject said visual images on said monitor while recording instances of device activation by said subject;
   (d) storing in said computer the instances of device activation by said subject;
   (e) determining an accuracy parameter of device activation;
   (f) determining a response time parameter of device activation;
   (g) calculating an Adjusted Accuracy as follows:

Adjusted Accuracy=Accuracy+10×(Latency−$R$)

where the value of R is selected to represent a typical response time value and Latency is the average response time of said subject, and wherein the adjusted accuracy discriminates between normal test results and abnormal test results characteristic of Attention Deficit Hyperactivity Disorder; and
   (h) using the calculation of step (g) to generate a report of said results.

4. The method of claim 2, wherein the Adjusted Latency is calculated using a typical accuracy value, Q, characteristic of said subject's gender.

5. The method of claim 2, wherein the Adjusted Latency is calculated using a typical accuracy value, Q, characteristic of said subject's age.

6. The method of claim 3, wherein the Adjusted Accuracy is calculated using a typical response time value, R, characteristic of said subject's gender.

7. The method of claim 3, wherein the Adjusted Accuracy is calculated using a typical response time value, R, characteristic of said subject's age.

8. The method of claim 1, further comprising the steps of:
   (h) using a motion analysis device connected to said computer to record movements of said subject during presentation of said visual images;
   (i) storing the record of said movements in said computer;
   (j) analyzing said recorded movements for abnormal deviations; and
   (k) using the analysis of step (j) together with the test value to diagnose Attention Deficit Hyperactivity Disorder.

9. The method of claim 2, further comprising the steps of:
   (h) using a motion analysis device connected to said computer to record movements of said subject during presentation of said visual images;
   (i) storing the record of said movements in said computer;
   (j) analyzing said recorded movements for abnormal deviations; and
   (k) using the analysis of step (j) together with the Adjusted Latency to diagnose Attention Deficit Hyperactivity Disorder.

10. The method of claim 3, further comprising the steps of:
    (h) using a motion analysis device connected to said computer to record movements of said subject during presentation of said visual images;
    (i) storing the record of said movements in said computer;
    (j) analyzing said recorded movements for abnormal deviations; and
    (k) using the analysis of step (j) together with the Adjusted Accuracy to diagnose Attention Deficit Hyperactivity Disorder.

11. The method of claim 8, 9 or 10, wherein said motion analysis device is a video camera.

12. The method of claim 11, wherein said camera is an infrared camera capable of detecting an infrared reflective marker.

13. The method of claim 12, wherein at least one infrared reflective marker is placed onto said subject.

14. The method of claim 1, 2, or 3, wherein said computer is connected to a second computer via a network and said instructions or said images are conveyed to said subject across the network.

15. The method of claim 14, wherein the network is selected from a global computer network, a local area network, a wide area network, an intranet, and an extranet.

16. The method of claim 1, 2, or 3, wherein said visual images are selected from the group consisting of symbols, numbers, letters, and shapes.

17. The method of claim 16, wherein said visual images are stars.

18. The method of claim 17, wherein said visual images are five-pointed stars and eight-pointed stars.

19. The method of claim 17, wherein said subject is instructed to activate said device when a star having a specified number of points is displayed on said monitor.

20. A method of diagnosing Attention Deficit Hyperactivity Disorder in a subject, said method comprising the steps of:
(a) placing, in proximity to a subject, (i) a monitor that is connected to a computer, and (ii) a device that can be activated by said subject and that is also connected to said computer;
(b) presenting to said subject instructions with respect to activating said device in response to visual images on said monitor, wherein said subject is instructed to activate said device when a specified image is displayed on said monitor;
(c) presenting to said subject said visual images on said monitor while recording instances of device activation by said subject;
(d) transmitting to a computer for analysis data from the instances of device activation by said subject; and
(e) receiving the results of said analysis, wherein said analysis comprises determining an accuracy parameter of device activation; determining a response time parameter of device activation; and calculating a test value based on said accuracy parameter and said response parameter as follows:

$$T=(accuracy)-[25+response\ time/10)],$$

wherein a positive value of T indicates a normal test result and a negative value of T indicates an abnormal test result characteristic of Attention Deficit Hyperactivity Disorder; and
(f) using said analysis to generate a report of said results.

21. A method of diagnosing Attention Deficit Hyperactivity Disorder in a subject, said method comprising the steps of:
(a) placing, in proximity to a subject, (i) a monitor that is connected to a computer, and (ii) a device that can be activated by said subject and that is also connected to said computer;
(b) presenting to said subject instructions with respect to activating said device in response to visual images on said monitor, wherein said subject is instructed to activate said device when a specified image is displayed on said monitor;
(c) presenting to said subject said visual images on said monitor while recording instances of device activation by said subject;
(d) transmitting to a computer for analysis data from the instances of device activation by said subject; and
(e) receiving the results of said analysis, wherein said analysis comprises determining an accuracy parameter of device activation; determining a response time parameter of device activation; and calculating an Adjusted Latency as follows:

$$Adjusted\ Latency=(response\ time)-10\times(accuracy-Q),$$

where the value of Q is selected to represent a typical accuracy value, and wherein the adjusted latency discriminates between normal test results and abnormal test results characteristic of Attention Deficit Hyperactivity Disorder; and
(f) using said analysis to generate a report of said results.

22. A method of diagnosing Attention Deficit Hyperactivity Disorder in a subject, said method comprising the steps of:
(a) placing, in proximity to a subject, (i) a monitor that is connected to a computer, and (ii) a device that can be activated by said subject and that is also connected to said computer;
(b) presenting to said subject instructions with respect to activating said device in response to visual images on said monitor, wherein said subject is instructed to activate said device when a specified image is displayed on said monitor;
(c) presenting to said subject said visual images on said monitor while recording instances of device activation by said subject;
(d) transmitting to a computer for analysis data from the instances of device activation by said subject; and
(e) receiving the results of said analysis, wherein said analysis comprises determining an accuracy parameter of device activation; determining a response time parameter of device activation; and calculating an Adjusted Accuracy as follows:

$$Adjusted\ Accuracy=Accuracy+10\times(Latency-R)$$

where the value of R is selected to represent a typical response time value and Latency is the average response time of said subject, and wherein the adjusted accuracy discriminates between normal test results and abnormal test results characteristic of Attention Deficit Hyperactivity Disorder; and
(f) using said analysis to generate a report of said results.

23. A method of diagnosing Attention Deficit Hyperactivity Disorder in a subject, said method comprising the steps of:
(I) providing data having been collected by the steps of (a) placing, in proximity to a subject, (i) a monitor can be activated to a computer, and (ii) a device that is controllable by said subject and that is also connected to said computer; (b) presenting to said subject instructions with respect to activating said device in response to visual images on said monitor, wherein said subject is instructed to activate said device when a specified image is displayed on said monitor; (c) presenting to said subject said visual images on said monitor while recording instances of device activation by said subject; and (d) recording the instances of device activation by said subject to produce said data;
(II) performing an analysis of said data, said analysis comprising determining an accuracy parameter of device activation; determining a response time parameter of device activation; and calculating a test value based on said accuracy parameter and said response parameter as follows:

$$T=(accuracy)-[25+response\ time/10)],$$

wherein a positive value of T indicates a normal test result and a negative value of T indicates an abnormal test result characteristic of Attention Deficit Hyperactivity Disorder; and
(III) using the analysis of step (II) to generate a report of said results.

24. A method of diagnosing Attention Deficit Hyperactivity Disorder in a subject, said method comprising the steps of:
(I) providing data having been collected by the steps of (a) placing, in proximity to a subject, (i) a monitor that is connected to a computer, and (ii) a device that can be activated by said subject and that is also connected to said computer; (b) presenting to said subject instructions with respect to activating said device in response to visual images on said monitor, wherein said subject is instructed to activate said device when a specified image is displayed on said monitor; (c) presenting to said subject said visual images on said monitor while recording instances of device activation by said subject; and (d) recording the instances of device activation by said subject to produce said data;

(II) performing an analysis of said data, said analysis comprising determining an accuracy parameter of device activation; determining a response time parameter of device activation; and calculating an Adjusted Latency as follows:

$$\text{Adjusted Latency} = (\text{response time}) - 10 \times (\text{accuracy} - Q),$$

where the value of Q is selected to represent a typical accuracy value, and wherein the adjusted latency discriminates between normal test results and abnormal test results characteristic of Attention Deficit Hyperactivity Disorder; and (III) using the analysis of step (II) to generate a report of said results.

25. A method of diagnosing Attention Deficit Hyperactivity Disorder in a subject, said method comprising the steps of:
   (I) providing data having been collected by the steps of (a) placing, in proximity to a subject, (i) a monitor that is connected to a computer, and (ii) a device that can be activated by said subject and that is also connected to said computer; (b) presenting to said subject instructions with respect to activating said device in response to visual images on said monitor, wherein said subject is instructed to activate said device when a specified image is displayed on said monitor; (c) presenting to said subject said visual images on said monitor while recording instances of device activation by said subject; and (d) recording the instances of device activation by said subject to produce said data;
   (II) performing an analysis of said data, said analysis comprising determining an accuracy parameter of device activation; determining a response time parameter of device activation; and calculating an Adjusted Accuracy as follows:

$$\text{Adjusted Accuracy} = \text{Accuracy} + 10 \times (\text{Latency} \times R)$$

where the value of R is selected to represent a typical response time value and Latency is the average response time of said subject, and wherein the adjusted accuracy discriminates between normal test results and abnormal test results characteristic of Attention Deficit Hyperactivity Disorder; and
   (III) using the analysis of step (II) to generate a report of said results.

26. The method of claim 21 or 24, wherein the Adjusted Latency is calculated using a typical accuracy value, Q, characteristic of said subject's age or gender.

27. The method of claim 22 or 25, wherein the Adjusted Accuracy is calculated using a typical response time value, R, characteristic of said subject's age or gender.

28. A method of diagnosing Attention Deficit Hyperactivity Disorder in a subject, said method comprising the steps of:
   (a) placing, in proximity to a subject, (i) a monitor that is connected to a computer, and (ii) a device that can be activated by said subject and that is also connected to said computer;
   (b) presenting to said subject instructions with respect to activating said device in response to visual images on said monitor, wherein said subject is instructed to activate said device when a specified image is displayed on said monitor;
   (c) presenting to said subject said visual images on said monitor while recording instances of device activation by said subject;
   (d) transmitting to a computer for analysis data from the instances of device activation by said subject; and
   (e) receiving the results of said analysis, wherein said analysis comprises determining an accuracy parameter of device activation; determining a response time parameter of device activation; calculating a composite test value based on said accuracy parameter and said response time parameter; and on the basis of said composite test value determining whether said test results are normal test results or abnormal test results characteristic of Attention Deficit Hyperactivity Disorder; and
   (f) using said analysis to generate a report of said results.

29. A method of diagnosing Attention Deficit Hyperactivity Disorder in a subject, said method comprising the steps of:
   (I) providing data having been collected by the steps of (a) placing, in proximity to a subject, (i) a monitor that is connected to a computer, and (ii) a device that can be activated by said subject and that is also connected to said computer; (b) presenting to said subject instructions with respect to activating said device in response to visual images on said monitor, wherein said subject is instructed to activate said device when a specified image is displayed on said monitor; (c) presenting to said subject said visual images on said monitor while recording instances of device activation by said subject; and (d) recording the instances of device activation by said subject to produce said data;
   (II) performing an analysis of said data, said analysis comprising determining an accuracy parameter of device activation; determining a response time parameter of device activation; calculating a composite test value based on said accuracy parameter and said response time parameter; and on the basis of said composite test value determining whether said test results are normal test results or abnormal test results characteristic of Attention Deficit Hyperactivity Disorder; and
   (III) using the analysis of step (II) to generate a report of said results.

* * * * *

UNITED STATES PATENT AND TRADEMARK OFFICE
CERTIFICATE OF CORRECTION

PATENT NO.         : 8,078,253 B2                                            Page 1 of 1
APPLICATION NO.    : 10/370809
DATED              : December 13, 2011
INVENTOR(S)        : Teicher et al.

It is certified that error appears in the above-identified patent and that said Letters Patent is hereby corrected as shown below:

Title Page 2, Item (56) under OTHER PUBLICATIONS, in Egan De, replace "Egan De." with
        --Egan, DE.--.

Column 13, Line 37, replace "(Latency×$R$)" with --(Latency-$R$)--.

Signed and Sealed this
Twelfth Day of March, 2013

Teresa Stanek Rea
*Acting Director of the United States Patent and Trademark Office*